US009652138B2

(12) United States Patent
Jones et al.

(10) Patent No.: US 9,652,138 B2
(45) Date of Patent: May 16, 2017

(54) SYSTEM AND METHOD FOR MULTI-TASKING OF A MEDICAL IMAGING SYSTEM

(71) Applicant: General Electric Company, Schenectady, NY (US)

(72) Inventors: Cheryl Ruth Jones, Hubertus, WI (US); John David Hoford, Pewaukee, WI (US); Tabb Alan Patz, New Berlin, WI (US); Mark Joseph Benson, Eagle, WI (US)

(73) Assignee: General Electric Company, Schenectady, NY (US)

( * ) Notice: Subject to any disclaimer, the term of this patent is extended or adjusted under 35 U.S.C. 154(b) by 277 days.

(21) Appl. No.: 14/617,998

(22) Filed: Feb. 10, 2015

(65) Prior Publication Data

US 2015/0169209 A1 Jun. 18, 2015

Related U.S. Application Data

(63) Continuation of application No. 13/106,923, filed on May 13, 2011, now Pat. No. 8,972,748.

(51) Int. Cl.

| | |
|---|---|
| ***H04L 29/06*** | (2006.01) |
| ***G06F 21/00*** | (2013.01) |
| ***G06F 3/0484*** | (2013.01) |
| ***A61B 6/03*** | (2006.01) |
| ***A61B 6/00*** | (2006.01) |
| ***G06F 19/00*** | (2011.01) |
| ***H04L 12/24*** | (2006.01) |

(52) U.S. Cl.
CPC ............ *G06F 3/04847* (2013.01); *A61B 6/03* (2013.01); *A61B 6/032* (2013.01); *A61B 6/467* (2013.01); *A61B 6/56* (2013.01); *G06F 19/321* (2013.01); *G06F 19/3418* (2013.01); *H04L 41/22* (2013.01)

(58) Field of Classification Search
CPC ......... G06F 21/60; G06F 19/321; A61B 6/03; A61B 6/467
See application file for complete search history.

(56) References Cited

U.S. PATENT DOCUMENTS 6,195,172 B1 * 2/2001 Minamizawa ..... H04N 1/00933 358/1.13
7,613,478 B2 11/2009 Jabri et al.
(Continued)

FOREIGN PATENT DOCUMENTS

| | | | |
|---|---|---|---|
| CN | 101164507 | A | 4/2008 |
| EP | 1857048 | A1 | 11/2007 |
| WO | 2007047457 | A2 | 4/2007 |

OTHER PUBLICATIONS

Unofficial English Translation of Chinese Office Action issued in connection with corresponding CN Application No. 201280023697.3 on Mar. 19, 2015.
(Continued)

*Primary Examiner* — Izunna Okeke

(57) ABSTRACT

A medical imaging system capable of acquiring medical imaging data of a patient includes a console coupled to the system, the console comprising a computer programmed to enable a first user to perform a first task on the system via the console, and enable a second user to perform a second task simultaneously with the first task via a remote device.

18 Claims, 3 Drawing Sheets

(56) References Cited

U.S. PATENT DOCUMENTS

| | | | | |
|---|---|---|---|---|
| 7,703,020 | B2 | 4/2010 | Bhattaru | |
| 8,284,208 | B2 | 10/2012 | Zaman et al. | |
| 2005/0251006 | A1 | 11/2005 | Dellis | |
| 2006/0255904 | A1 | 11/2006 | Danzer et al. | |
| 2010/0082842 | A1 | 4/2010 | Lavrov et al. | |
| 2011/0288853 | A1* | 11/2011 | Butzine | A61B 6/4405 704/8 |

OTHER PUBLICATIONS

Search Report and Written Opinion from related PCT Application No. PC1/US2012/037492 dated Aug. 8, 2012.

* cited by examiner

SYSTEM AND METHOD FOR MULTI-TASKING OF A MEDICAL IMAGING SYSTEM

CROSS-REFERENCE TO RELATED APPLICATION

The present application is a continuation of and claims priority to U.S. patent application Ser. No. 13/106,923 filed May 13, 2011, the disclosure of which is incorporated herein in its entirety.

BACKGROUND

Embodiments of the invention relate generally to diagnostic imaging and, more particularly, to a method and apparatus of multi-tasking on a medical diagnostic imaging system.

Diagnostic imaging systems may include computed tomography (CT) imaging systems, magnetic resonance imaging systems, x-ray systems, and PET systems, as examples. The invention described herein is described with respect to a CT system, however it is contemplated that the invention may be applicable to any imaging system.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image. The x-ray source and detector are mounted on a gantry, which rotates about the subject while the patient is axially conveyed through a center of the gantry.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction. As such, imaging data is obtained of the subject while the subject is axially conveyed through the gantry.

The CT system is operated and data is acquired from the system using a console that is located in close proximity to the gantry. A user may use the console for accessing patient data or images, entering patient data, defining diagnostic procedures, and the like. The user may also use the console for running an imaging session and analyzing imaging data as well.

Currently, if a single user is using the medical diagnostic system, a second user must typically either interrupt the workflow of the first user to complete their task, or wait until the first user has completed their task, in either case delaying the completion of the diagnostic procedure. Thus, if the first user is using the system for, for instance, imaging data acquisition, the first user must be interrupted in order for the second user to access for instance information about the patient, or to enter information about a subsequently planned imaging procedure on the next patient. The interruptions can cause mistakes to be made in data imaging, data entry, and such, and cause system downtime and overall inefficient use of equipment.

Attempts have been made to solve this problem by displaying a separate floating window on a user interface of a console, and providing additional dedicated hardware such as a touchscreen, a mouse, or a trackball to allow interaction from a second user. Other attempts to solve the problem include locating a separate display in a second location and using a video cable to access information from the console. However, such systems can be expensive and can nevertheless result in distractions to a user of a console.

Therefore, it would be desirable to design an apparatus and method for more efficiently operating a diagnostic imaging system.

BRIEF DESCRIPTION

The invention is a directed method and apparatus for multi-tasking of a medical imaging system.

According to an aspect of the invention, a medical imaging system capable of acquiring medical imaging data of a patient includes a console coupled to the system, the console comprising a computer programmed to enable a first user to perform a first task on the system via the console, and enable a second user to perform a second task simultaneously with the first task via a remote device.

According to another aspect of the invention, a method of accessing a medical diagnostic system includes performing a first task on the medical diagnostic system by a first user using a console, and while performing the first task, performing a second task on the medical diagnostic system by a second user using a portable electronic device to communicate with the medical diagnostic device.

According to yet another aspect of the invention, a non-transitory computer readable storage medium having stored thereon a computer program comprising instruction which, when executed by a computer, cause the computer to access a first medical diagnostic imaging system, enable a first user to perform a first task on the first medical diagnostic imaging system via a console that is configured to control operation of the first medical diagnostic imaging system, and receive information from a wireless device to concurrently perform a second task on the first medical diagnostic imaging system.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Imaging devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. It will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy and for other medical imaging systems in general. An implementation is employable with a "third generation" CT scanner and/or other CT systems.

The operating environment of the present invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
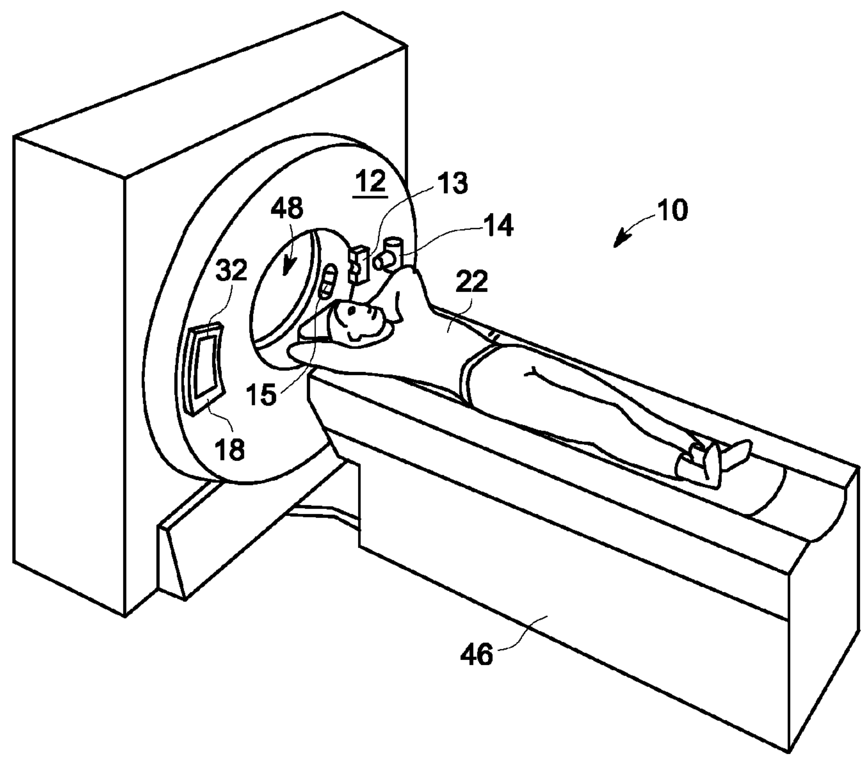
FIG. 1 is a pictorial view of a CT imaging system.
Figure 2:
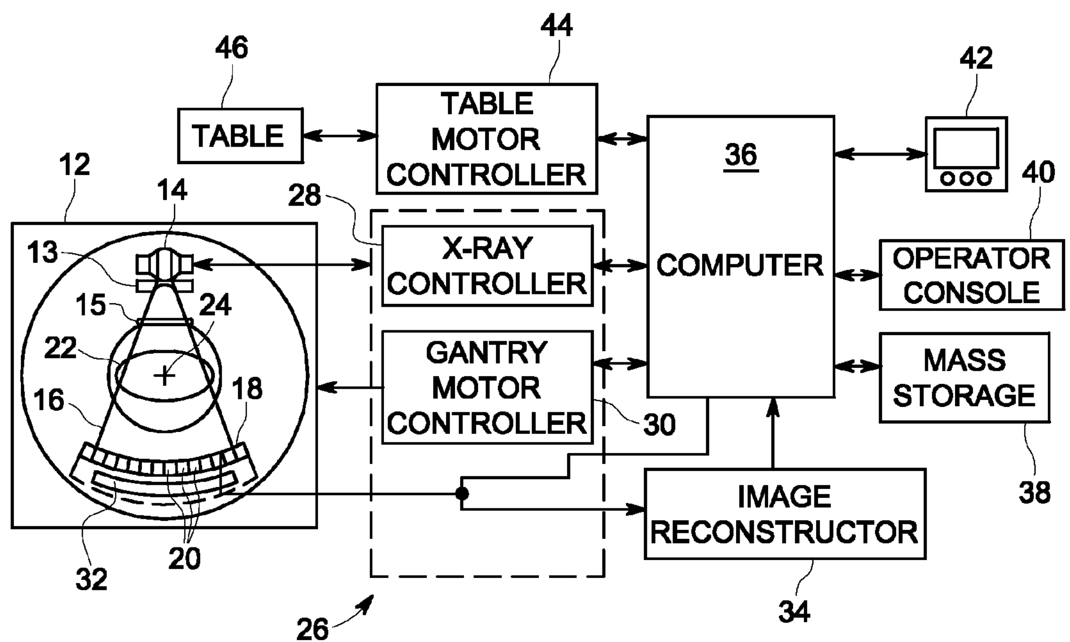
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 through a bowtie filter 13 and toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
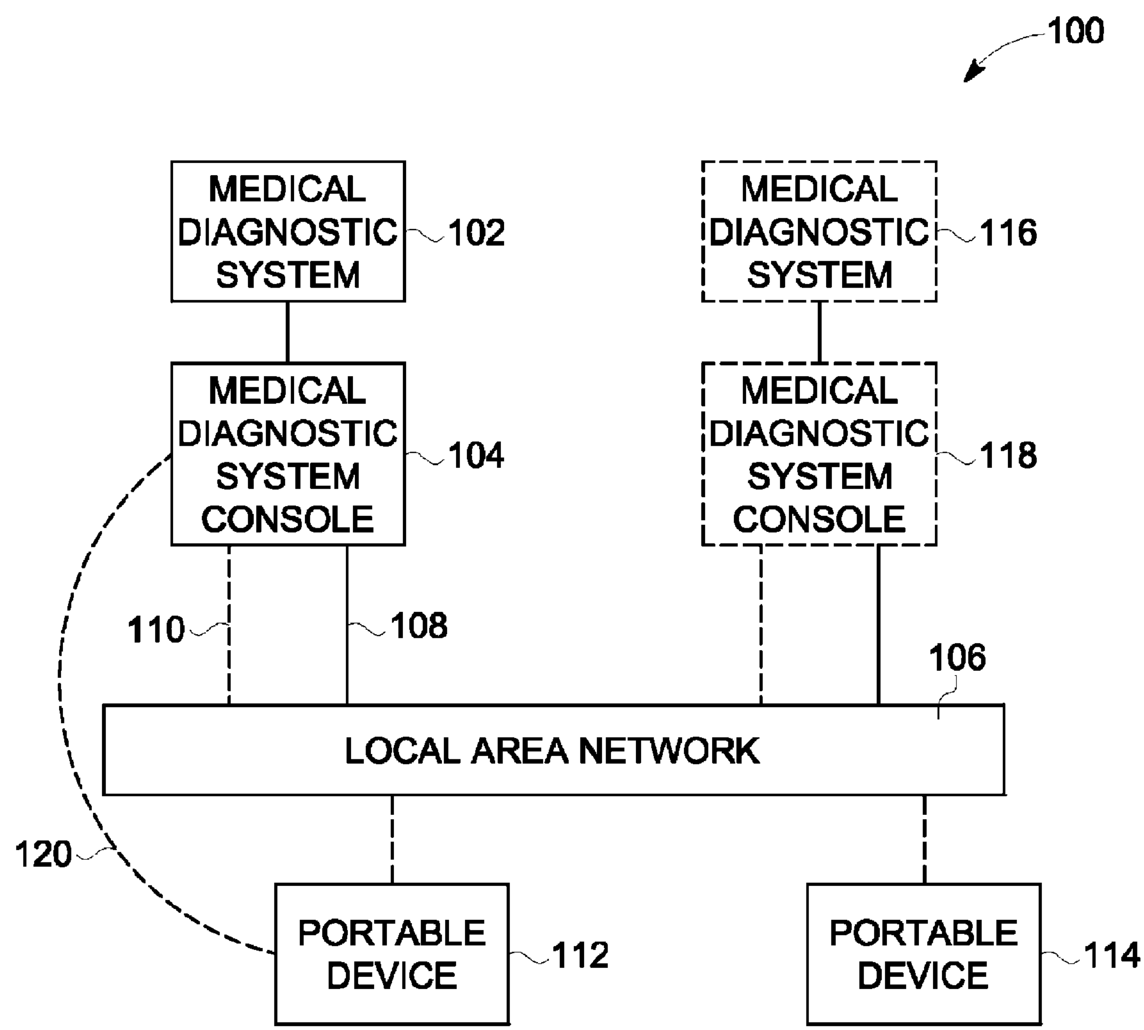
FIG. 3 is a block schematic diagram of a medical imaging system accessed via a portable device according to an embodiment of the invention.

Referring now to FIG. 3, a networked system of imaging devices 100 includes a medical diagnostic system 102 which includes a medical diagnostic system console 104. Medical diagnostic system 102 in one embodiment is a CT system, such as CT imaging system 10 as illustrated in FIGS. 1 and 2, and in that embodiment medical diagnostic system console 104 is operator console 40 as illustrated in FIG. 2. However, as stated, medical diagnostic system 102 is not limited to a CT system and may be any imaging system which obtains imaging data of an object, is controlled and accessed from a computer terminal, and may be accessed via a remote device.

Medical diagnostic system console 104 in one embodiment is connected to a local area network (LAN) 106 or to any broadband-type connectivity. In one embodiment LAN 106 is hard-wired to medical diagnostic system console 104 via a communication cable 108. In another embodiment LAN 106 is configured to communicate with medical diagnostic system console 104 wirelessly 110, precluding the use of communication cable 108. According to the invention, a remote or portable device 112 may be operated proximate LAN 106, and may be used to access medical diagnostic system 102 by one user via LAN 106 wirelessly and remotely, while another user is simultaneously accessing medical diagnostic system 102 using medical diagnostic system console 104.

Console 104 may include, as examples, a monitor for displaying imaging information, patient information, scanning protocol information, and the like. Console 104 may also include a keyboard and/or mouse for accessing a computer, such as computer 36 of imaging system 10. In embodiments of the invention, portable device 112 is one of a tablet PC, a smart phone, a portable media player, and a purpose-built device (i.e., a remote device fabricated explicitly for the purpose of wirelessly and remotely accessing medical diagnostic system 102). One skilled in the art will recognize that portable device 112 may be any device that may be wirelessly coupled to, for instance, another device, and is not limited to the listed device types.

It is contemplated that numerous tasks may be performed on medical diagnostic system 102 using medical diagnostic system console 104 or portable device 112. For instance, tasks that may be performed include but are not limited to processing imaging data, viewing imaging data, displaying a patient list, displaying next patient information, editing patient data, displaying non-imaging medical information of the patient, displaying a procedure to be performed, displaying an indication that a next patient is ready for imaging, displaying an owner's manual of the medical imaging system, administering x-rays, and monitoring a state of the imaging system. That is, a first user may perform a first task on medical diagnostic system 102 using medical diagnostic system console 104, and a second user may perform a second task using portable device 112. In such fashion and in this example, the first user may be preparing to image a patient and may continue to uninterruptedly do so while the second user may be accessing medical diagnostic system 102 to edit patient data.

Console 104 may be arranged or have a computer programmed to ensure that system console 104 has an overriding command capability in order to control what level of control of, or access to, system 102, is allowed via portable device 112. Thus, according to the invention system console 104 may be used to de-feature functionality of portable device 112, or to prevent portable device 112 from accessing system 102 at all. Additionally, system console 104 may be configured to notify the first user that a portable device such as portable device 112 is accessing medical diagnostic system 102. System console 104 may also be configured to display an option for the first user to select in order to prevent the second task from being performed or to prevent access at all from portable device 112, to provide security and prevent access from an unauthorized user, to display a warning when the second task is about to be performed, disable the remote device based on its location, and to encrypt/decrypt data sent to/received from the remote device, as examples.

Thus, networked system of imaging devices 100 allows a portable device to have limited features compared to those of the main console, such as console 104. For example, portable device 112 may be prevented from an ability to control or change specific parameters of a diagnostic procedure (such as an ability to administer x-rays) or move some portion of the medical device. Or, in one embodiment, such features may be allowed but only after approval is obtained through a main console such as console 104.

As stated, medical diagnostic system 102 may include a computer such as computer 36 of system 10 illustrated in FIGS. 1 and 2. Thus, additional software features may be incorporated in medical diagnostic system 102 to include, for instance, an encryption/decryption ability between console 104 and portable device 112. In such fashion, data may be prevented from being intercepted or understood from an undesirable additional wireless receiver in order to protect patient privacy.

According to the invention, multiple portable devices may be used to access medical diagnostic system 102. That is, portable device 112 may be used to access system 102 while the first user is accessing system 102 via system console 104, and another portable device 114 may also be used to simultaneously access system 102 as well. As with portable device 112, portable device 114 may include any device type as described, and functionality may be limited as well. Further, the types of devices 112 and 114 may be different from one another (that is, one may be a tablet PC while another may be a smart phone).

Portable devices 112, 114 may be configured to alert one another of tasks being performed by the other portable device. For instance, in one example a user may access medical diagnostic system 102 via portable device 112 in order to prepare medical diagnostic system 102 for the next patient to be imaged. However, due to miscommunication or for other reasons, another user may attempt to access medical diagnostic system 102 using portable device 114 to perform the same task. Thus, according to the invention, the user with portable device 112 may be alerted to the presence of portable device 114, and may further be alerted to the fact that a user with portable device 114 is attempting to perform the same task. In addition, according to the invention and with this example, a user at console 104 may be likewise alerted to the activity on both portable devices 112, 114 and may be offered an override command to stop one or both devices 112, 114 from accessing medical diagnostic system 102 and performing any tasks.

It is contemplated that multiple imaging systems may be accessed remotely by portable devices as well. Referring still to FIG. 3, another medical diagnostic system 116 may be included as well, having a respective medical diagnostic system console 118. Thus, as with medical diagnostic system 102, medical diagnostic system 116 may likewise be accessed by one or more portable devices such as devices 112, 114, and similar functionality may be imparted to system 116 as is to system 102. Further, in an embodiment that includes more than one diagnostic system, it is contemplated that a single device such as portable device 112 may be used to separately access each system 102, 116, simultaneously while users at respective consoles 104, 118 access and use systems 102, 116 as well.

Further, in a networked system 100 having multiple imaging systems such as systems 102, 116 and respective consoles 104, 118, an alarm or warning may be sent to a remote user that is wirelessly accessing one imaging system but while in close proximity to another imaging system. As an example, a user accessing medical diagnostic system 102 may do so using portable device 112 but while standing proximate, for instance, medical diagnostic system 116. The user may desire to do this in order to, for instance, download data from medical diagnostic system 102 or check status of an imaging session on medical diagnostic system 102, while at the same time working with another user that is imaging a patient on medical diagnostic system 116. Thus, using proximity sensors or GPS systems to determine the location of the user, the user of portable device 112 who is standing near medical diagnostic system 116 may be warned that medical diagnostic system 102 is the system being accessed. Such a warning could serve to prevent the user from inadvertently thinking he/she is accessing one system (system 116) while they are really accessing another system (102).

Networked system 100 may be configured in a fashion to forego the use of LAN 106. Thus, according to an embodiment of the invention, a remote device such as portable device 112 and medical diagnostic system console 104 may be configured such that portable device 112 accesses medical diagnostic system console 104 wirelessly 120.

Figure 4:
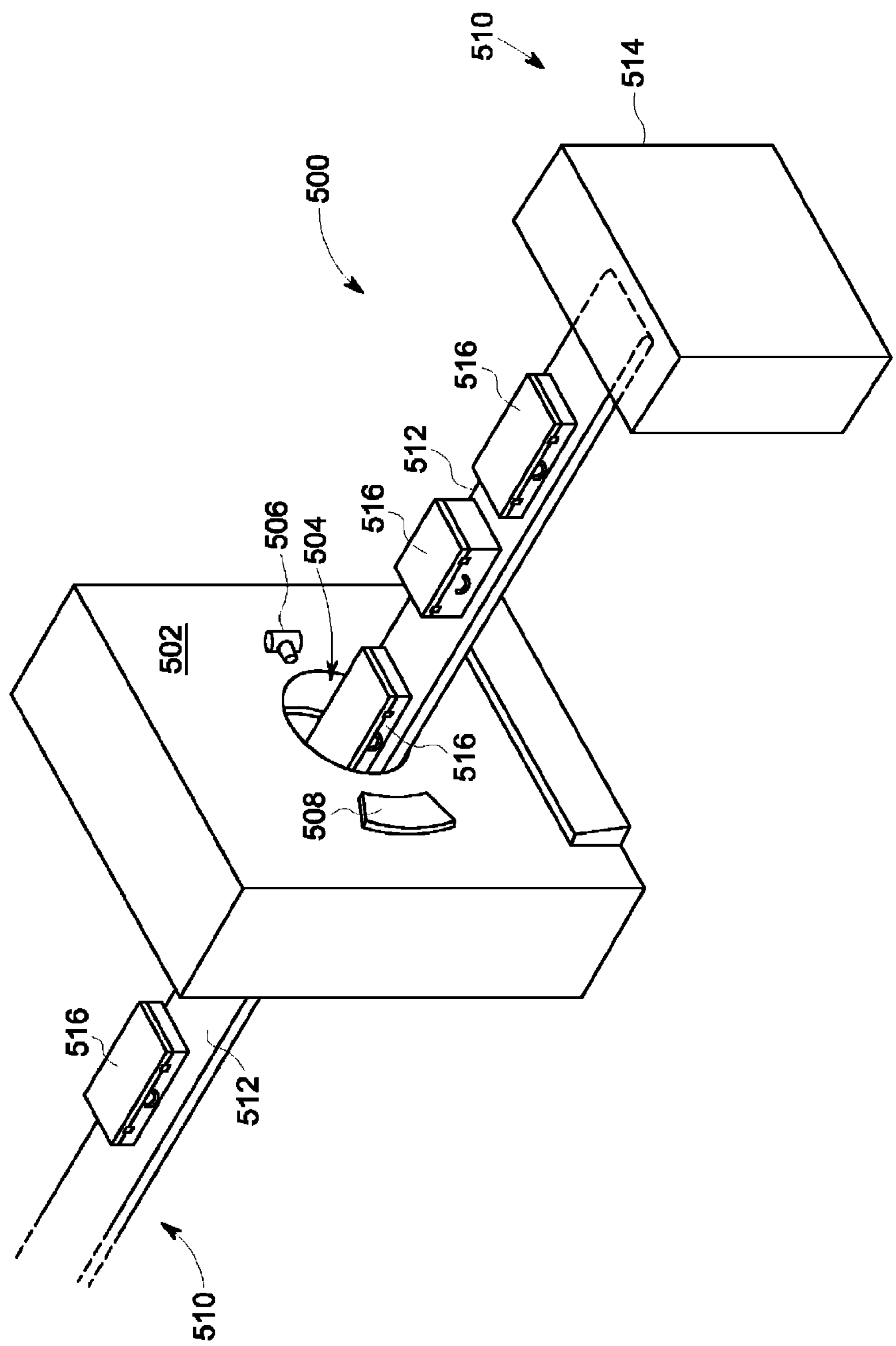
FIG. 4 is a pictorial view of a CT system for use with a non-invasive package inspection system.

Referring now to FIG. 4, package/baggage inspection system 500 includes a rotatable gantry 502 having an opening 504 therein through which packages or pieces of baggage may pass. The rotatable gantry 502 houses an x-ray and/or high frequency electromagnetic energy source 506 as well as a detector assembly 508 having scintillator arrays comprised of scintillator cells. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc. An exemplary implementation can aid in the development of automatic inspection techniques, such as explosive detection in luggage.

A technical contribution for the disclosed method and apparatus is that it provides for a computer implemented method and apparatus of multi-tasking on a medical diagnostic imaging system.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to an embodiment of the invention, a medical imaging system capable of acquiring medical imaging data of a patient includes a console coupled to the system, the console comprising a computer programmed to enable a first user to perform a first task on the system via the console, and enable a second user to perform a second task simultaneously with the first task via a remote device.

According to another embodiment of the invention, a method of accessing a medical diagnostic system includes performing a first task on the medical diagnostic system by a first user using a console, and while performing the first task, performing a second task on the medical diagnostic system by a second user using a portable electronic device to communicate with the medical diagnostic device.

According to yet another embodiment of the invention, a non-transitory computer readable storage medium having stored thereon a computer program comprising instruction which, when executed by a computer, cause the computer to access a first medical diagnostic imaging system, enable a first user to perform a first task on the first medical diagnostic imaging system via a console that is configured to control operation of the first medical diagnostic imaging system, and receive information from a wireless device to concurrently perform a second task on the first medical diagnostic imaging system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A medical imaging system capable of acquiring medical imaging data of a patient, the system comprising:
- a console coupled to the system, the console comprising a computer programmed to:
- enable a first user to perform a first task on the medical imaging system via the console; and
- enable a second user to perform a second task on the medical imaging system simultaneously with the first task via a remote device;
- wherein, in enabling the second user to perform the second task on the medical imaging system via the remote device, the computer is programmed to:
- encrypt data sent to the remote device; and decrypt data received from the remote device; and
- wherein the computer is programmed such that the console has an overriding command capability to limit functionality of the remote device, and to prevent access of the remote device to the medical imaging system such that the second task cannot be performed.

2. The medical imaging system of claim 1 wherein the computer is programmed to alert the second user if the second user is more proximate to another medical imaging system than to the console.

3. The medical imaging system of claim 1 wherein the computer is programmed to enable the second task to be performed via the remote device by using at least one of a local area network (LAN) and a broadband connectivity device coupled between the remote device and the console.

4. The medical imaging system of claim 1 wherein the computer is programmed to enable the remote device to be directly coupled wirelessly with the console.

5. The medical imaging system of claim 1 wherein the remote device comprises a tablet PC, a smart phone, a portable media player, and a purpose-built device.

6. The medical imaging system of claim 1 wherein one of the first task and the second task comprises one of processing imaging data, viewing imaging data, displaying a patient list, displaying next patient information, editing patient data, displaying non-imaging medical information of the patient, displaying a procedure to be performed, displaying an indication that a next patient is ready for imaging, displaying an owner's manual of the medical imaging system, administering x-rays, and monitoring a state of the imaging system.

7. The medical imaging system of claim 1 wherein the computer is programmed to notify the first user that the remote device is enabled to perform the second task.

8. The medical imaging system of claim 7 wherein the computer is programmed to perform at least one of:
- display an option for the first user to select in order to prevent the second task from being performed;
- display a warning when the second task is about to be performed; and
- disable the remote device based on its location.

9. The medical imaging system of claim 1 wherein the computer is programmed to enable a third user to perform a third task simultaneously with the first task and the second task via another remote device.

10. The medical imaging system of claim 9 wherein the computer is programmed to alert one of the first user and the second user when the third task is being prepared to be performed by the third user, and to enable one of the first user and the second user to prevent the third task from being performed.

11. A non-transitory computer readable storage medium having stored thereon a computer program comprising instruction which, when executed by a computer, cause the computer to:

access a medical diagnostic imaging system;

receive a first command to perform a first task on the medical diagnostic imaging system from a console that is configured to control operation of the medical diagnostic imaging system; and receive a second command from a wireless device to perform a second task on the medical diagnostic imaging system;

wherein, in receiving the second command from the wireless device, the computer is programmed to:

encrypt data sent to the wireless device; and decrypt data received from the wireless device; and wherein the computer is programmed such that the console has an overriding command capability to limit functionality of the remote device, and to prevent access of the remote device to the medical imaging system such that the second task cannot be performed.

12. The computer readable storage medium of claim 11 wherein the instructions further cause the computer to:

enable a first user to control a first aspect of the diagnostic procedure via the console; and simultaneously enable the second user to control a second aspect of the diagnostic procedure via the wireless device.

13. The computer readable storage medium of claim 11 wherein the wireless device is configured to receive the second task input via a second user.

14. The computer readable storage medium of claim 11 wherein the instructions further cause the computer to perform one of:

enable the first user to restrict an ability of the wireless device to perform the second task;

display a warning to the first user when the second task is about to be performed;

disable the wireless device based on its location; and decrypt data received from the wireless device.

15. The computer readable storage medium of claim 11 wherein the instruction further provides an overriding command option to the first user that prevents other users from accessing the medical diagnostic imaging system.

16. A system comprising:

a medical imaging system capable of acquiring medical imaging data of a patient;

a console coupled to the medical imaging system, the console comprising a computer programmed to provide a first command to the medical imaging system to perform a first task, the first command being provided responsive to an input to the console by a first user;

wherein the computer is programmed to:

encrypt data sent to the remote device; and decrypt data received from the remote device and a remote device in wireless communication with the medical imaging system, the remote device configured to provide a second command to the medical imaging system to perform a second task, the second command being provided responsive to an input to the remote device by a second user; and wherein the computer is programmed such that the console has an overriding command capability to limit functionality of the remote device, and to prevent access of the remote device to the medical imaging system such that the second task cannot be performed.

17. The system of claim 16 wherein the console and the remote device provide for the first task to be performed simultaneously with the second task.

18. The system of claim 16 wherein the computer is programmed to enable the second task to be performed via the remote device by using at least one of a local area network (LAN) and a broadband connectivity device coupled between the remote device and the console.

* * * * *